United States Patent [19]

Usry et al.

[11] Patent Number: 4,588,425
[45] Date of Patent: May 13, 1986

[54] HUMIDIFIER

[75] Inventors: Joe Usry, Midvale; Roger Atkins, Salt Lake City; Chris Faddis, West Valley City, all of Utah

[73] Assignee: Bunnell Life Systems, Inc., Salt Lake City, Utah

[21] Appl. No.: 716,199

[22] Filed: Mar. 26, 1985

Related U.S. Application Data

[63] Continuation of Ser. No. 549,789, Nov. 8, 1983, abandoned.

[51] Int. Cl.$^4$ .............................................. B01D 47/00
[52] U.S. Cl. ................................... 55/227; 55/249; 55/256; 55/267; 128/200.21; 128/203.27; 261/142; 261/DIG. 54
[58] Field of Search ................. 55/227, 248, 249, 256, 55/257 QN, 95, 257 PV, 267; 128/200.21, 203.27; 219/272, 273; 239/338, 398, 433; 261/121 R, 142, DIG. 54

[56] References Cited

U.S. PATENT DOCUMENTS

| 813,217 | 2/1906 | Kinealy | 55/257 PV |
|---|---|---|---|
| 3,495,440 | 2/1970 | Koblin et al. | 55/95 X |
| 3,884,653 | 5/1975 | Capulli et al. | 261/121 R |
| 3,982,095 | 9/1976 | Robinson | 261/142 |
| 4,152,379 | 5/1979 | Suhr | 261/142 |
| 4,267,974 | 5/1981 | Kionholz et al. | 261/142 |
| 4,312,646 | 1/1982 | Fattinger et al. | 55/227 |
| 4,346,048 | 8/1982 | Gates | 261/142 |
| 4,439,215 | 3/1984 | Rawicki | 55/227 |

Primary Examiner—Charles Hart
Attorney, Agent, or Firm—Thorpe, North & Western

[57] ABSTRACT

A humidifier for pulmonary assistance systems which includes a transparent housing with an air passage extending therethrough and water reservoir. The passage includes a convergent-divergent section separated by a narrow throat. A narrow channel connecting the reservoir to the throat so that with the divergent section being open to the reservoir, the differential pressure between the reservoir and the throat causes water to flow into the air passage. A collection surface is provided in the divergent section for extracting water droplets from the air flowing through the passage, and a heating panel is provided for heating the water in the reservoir.

12 Claims, 4 Drawing Figures

HUMIDIFIER

This application is a continuation of application Ser. No. 549,789 filed Nov. 8, 1983, and now abandoned.

BACKGROUND OF THE INVENTION

The present invention relates to a humidifier and more particularly to a humidifier especially adapted for use in pulmonary assistance systems.

In pulmonary assistance systems wherein air, oxygen and/or medication are supplied to augment or enhance a patient's normal breathing, it often becomes desirable to add moisture to the air supplied to the patient. Heretofore, this has been accomplished by channeling the air being supplied past a container of water. The container is heated to raise the temperature of the water to increase the vaporization and the air is then passed over the water or a water-filled curtain, such as a wick, and water vapor is entrained in the air flow. Such devices have been designed for use at low pressures and at normal breathing rates and have been relatively large to meet the breathing needs of the user. In assistance systems which utilize a rapid sequence of short pulses of pressurized air or oxygen to achieve deep penetration within the pulmonary tract, the gas volume within the humidifier must be limited to ensure transmission of the high frequency pulses through the humidifier. If the gas volume within the humidifier exceeds a certain level, the high frequency pulses will be damped out within the humidifier rather than being transmitted to the patient. In addition, high frequency ventilation necessitates the use of higher pressures than occur at normal ventilation, so the humidifier apparatus must be a pressure vessel. The prior known devices generally do not meet these requirements and are, therefore, not suitable for use with high frequency ventilation systems.

SUMMARY OF THE INVENTION

The present invention provides a humidifier for pulmonary assistance systems and utilizes the principle of a jet pump to draw water from a reservoir and entrain it as vapor in air flowing through the apparatus. A collection surface is provided for extracting droplets of water from the air flow and returning them to the reservoir. The humidifier is packaged in a transparent housing which includes a heating panel to enhance the vaporization of the water and to permit visual observation of the humidifying process to ensure proper function of the apparatus.

BRIEF DESCRIPTION OF THE DRAWINGS

The best mode presently contemplated for carrying out the invention will be understood from the detailed description of the preferred embodiments illustrated in the accompanying drawings in which.

DETAILED DESCRIPTION

Figure 1A:
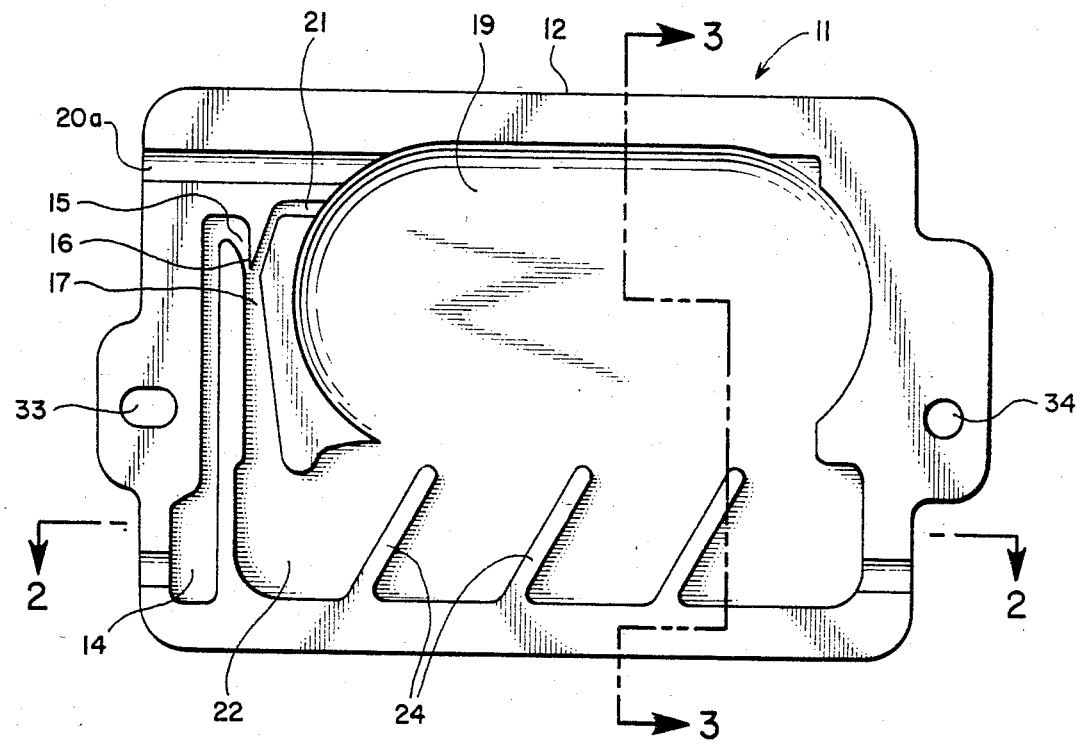
FIGS. 1A and 1B show respectively a side elevation view of a front section and back section of a humidifier housing made in accordance with the present invention.
Figure 1B:
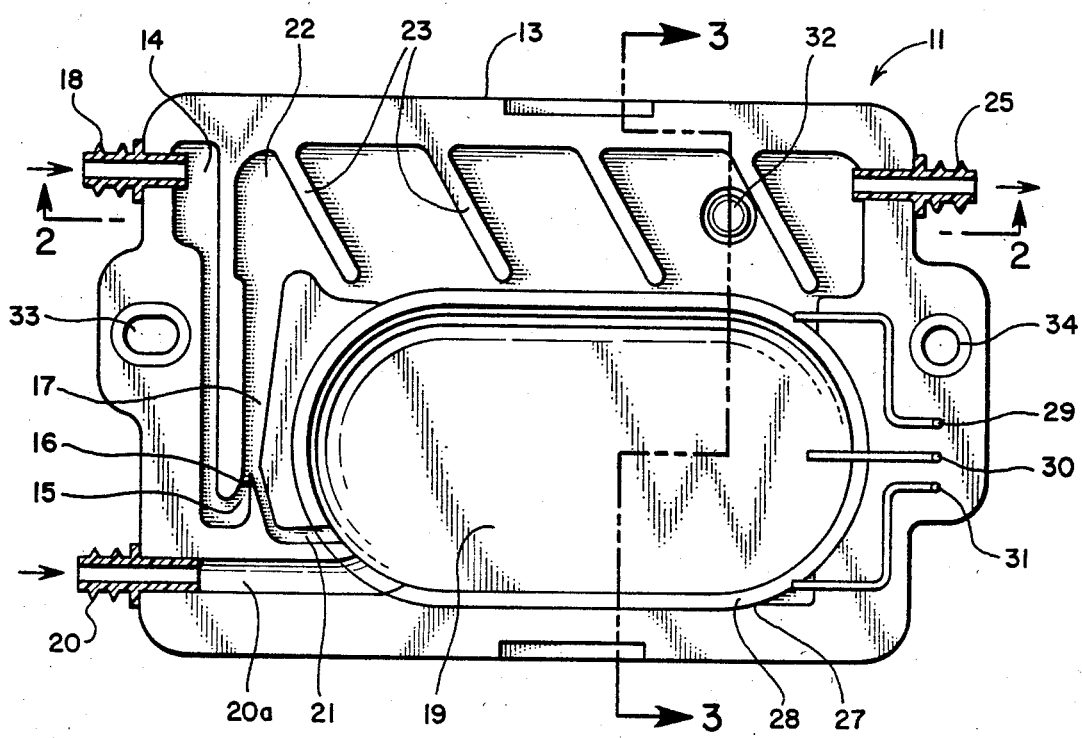
Figure 2:
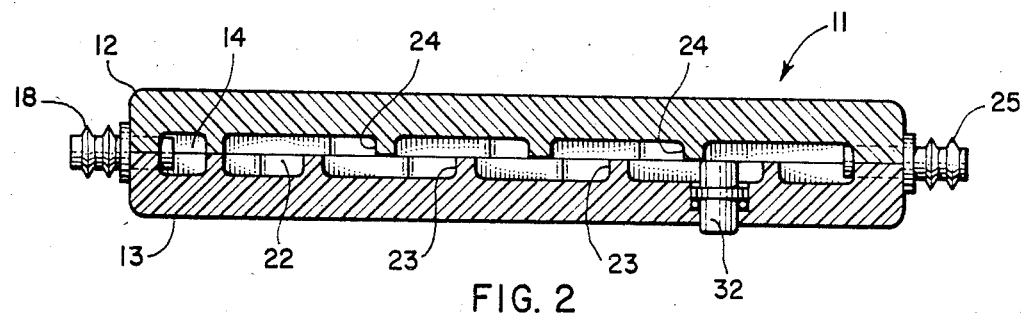
FIG. 2 is a top view of the humidifier of composite FIG. 1.
Figure 3:
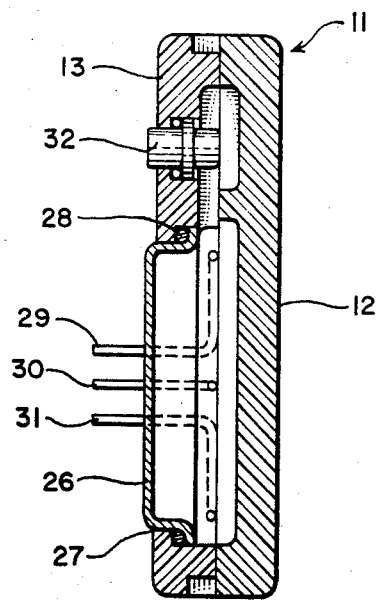
FIG. 3 is an end view of the humidifier of composite FIG. 1.

The present invention avoids the disadvantages and deficiencies of the prior known devices by provision of a humidifier which has a minimum gas volume and is, thus, compact in size, and is capable of use with high frequency pulmonary assistance systems, the function of which is observable during operation. As shown in the drawings, a housing 11 includes a front section 12 joined to a back section 13 by a suitable bond (FIGS. 1A and 1B show the sections laid open similar to a book with the section in FIG. 1A being upside down and the section in FIG. 1B being right side up.). The housing has the general shape of a rectangular prism and is formed of a suitable thermoplastic material which is transparent. An air passage 14 is formed in the interior of the housing and is provided with a venturi section which includes an upstream convergent segment 15, a narrow throat 16 and a downstream divergent segment 17. A source of air under pressure is connected to passage 14 through an air inlet connector 18 in the upstream end of the housing. Due to the venturi effect of air passing through the convergent segment 15, the velocity of air passing through the throat 16 is increased, while the pressure of the air in the throat is correspondingly decreased. Conversely, in the divergent section 17 the velocity of the air flow is reduced and the pressure correspondingly increased.

A reservoir 19 is formed centrally in the housing and is supplied with water through a connection 20 and channel 20a in the upstream end of the housing. The upper portion of the reservoir is open to a portion of the air passage 14 so that the surface of the water is exposed to the pressure of the air therewithin. The pressure differential between the surface of the water in the reservoir and the throat 16, combined with the aspirating effect of the air flow past the end of a channel 21, causes water to flow from the reservoir, through the channel 21, into the throat. The position of the venturi section below the water level in the reservoir facilitates water pick up in a pulsing mode. The water discharged from channel 21 into the rapidly moving air flow in the throat is entrained in the flow and largely vaporized.

The divergent segment 17 discharges into an enlarged scrubbing area 22 which extends over the length of the reservoir along its upper edge. A series of vanes 23 and 24 extend across the scrubbing area from the upper edge of the housing to the upper edge of the reservoir and are angled approximately 30° in the direction of air flow. Alternate vanes are formed on the front and back sections of the housing as shown in the drawings to provide a sinuous path through the area 22. As the air flows through the scrubbing area, its strikes the vanes 23, 24, etc., which serve as collection surfaces. As the air flows through the scrubbing area, the droplets of water are propelled against the vanes and will collect thereon. Due to the angular position of the vanes, the momentum of the air stream against the collected droplets forces them to move down the vanes and drop back into the reservoir faster than the gravity pull. The number of vanes and spacing between them are chosen such that all of the entrained droplets are cleared from the air flow before it is discharged through outlet 25 at the downstream end of the housing.

The air passage 14 through the housing is configured such that the venturi section is located below the water level in the reservoir and the discharge from the divergent segment 17 is vectored away from the reservoir. The location of the venturi insures that water will always be present at the throat 16 for entrainment in either a continuous or pulsing mode of operation. Vectoring the discharge from the divergent segment against the housing (vanes) rather than against the reservoir prevents formation of waves on the surface of the water in the reservoir which would cause entrainment of water droplets within the scrubbing area and consequent spitting at the outlet 25.

A lateral wall of the reservoir 19 on the back section 13 is formed by a flat cup 26 made of heat conductive material, such as aluminum, copper, etc., which is retained in sealing relation within an opening 27 in the section by means on an O-ring 28. The water within the reservoir is heated by application of heat to the cup 26.

The water level in the reservoir 19 is sensed by a sensor which includes electrically conductive pins 29, 30 and 31 which extend through the back section of the housing into the reservoir and are spaced to detect half-full and full conditions in the reservoir. The half-full indication is detected when water covers pins 30 and 31 to, for example, close a circuit, and is used to prevent application of heat to the reservoir until it is half filled with water. The full level indication is detected when water covers pins 29 and 30, and is used to signal a water supply pump to pump water into the reservoir against the pressure within the housing to thereby maintain the water level at the desired point. When the reservoir is full, the heater will operate at optimum efficiency and the gas volume within the housing will be maintained at some predetermined level, advantageously between 0.5 and 1.5 cubic inches.

A temperature sensor 32 is installed in the scrubbing area close to the outlet 25 to sense the temperature of the air flow so that the heater can be regulated to maintain the water at the desired temperature with different rates of air flow. The sensor could be a conventional thermocouple temperature sensing device.

The front and back sections of the housing can be molded of clear plastic in an injection molding machine. The grooves and recesses in the facing surfaces of the front and back sections match with one another to define the various openings, passages, etc. when the sections are joined. The metal cup 26 can be stamped from sheet material and pushed into place in the back section before the two sections are joined. The manufacture and assembly is simple and inexpensive, so that the humidifier can be discarded after use instead of being disassembled and sterilized.

The humidifier apparatus can be mounted on a control box with the aid of two guide pins received in openings 33 and 34 in the opposite ends of the housing. Latches can be utilized to hold the housing in place on the pins. The cup 26 on the back of the housing presses against a spring-loaded heater plate for good thermal contact. When the latches are released, the used humidifier can be removed from the pins. A new one is installed by placing the housing on the pins and pressing down until the latches snap in place.

The present humidifier can operate continuously or intermittently, as desired, can produce humid air in small quantities, and removes the entrained water droplets so that the moisture is delivered only in the form of water vapor. The transparent housing permits the function of the humidifier to be visually checked during the operation to detect any problems which might occur.

While the invention has been described with reference to specifically illustrated preferred embodiments, it should be realized that various changes may be made without departing from the disclosed inventive subject matter particularly pointed out and claimed herebelow.

What is claimed is:

1. A humidifier which includes
    a housing having an air passage defined therein, said air passage including
        a venturi section comprising a convergent segment, a narrow throat, and a divergent segment, and
        a scrubber area for receiving air and water vapor from the divergent segment,
    a water reservoir defined in the housing at a location below the scrubber area to receive water droplets therefrom, and such that the venturi section is below the water level in the reservoir,
    a narrow channel connecting the reservoir with the throat of the venturi section to carry water to the venturi section to thereby vaporize at least a portion of the water,
    means for heating water in the water reservoir, and
    wherein the housing includes two plates of transparent plastic positioned in a side-by-side relationship, with the air passage and reservoir being defined in facing surfaces of the plates.
2. A humidifier as defined in claim 1 further including a series of vanes extending generally parallel to one another across a substantial portion of the scrubber area and wherein the divergent segment discharges against an inner surface of the housing.
3. A humidifier as defined in claim 1 wherein the heating means includes
    a metal cup fitted into one of the plates to define a side wall of the reservoir.
4. A humidifier as defined in claim 1 wherein the gas volume within the housing is between about 0.5 and 1.5 cubic inches.
5. A humidifier as defined in claim 4 further including means for sensing the level of water in the reservoir.
6. A humidifier as defined in claim 1 further including means for sensing the temperature of the humidified air in the air passage.
7. A humidifier as in claim 2 wherein said vanes are formed to extend downwardly from near the top of the housing into the scrubber area alternately from opposite sides of the scrubber area to define a sinuous path of travel for the air flow.
8. A humidifier as in claim 7 wherein said vanes are formed to extend downwardly at an acute angle from the vertical in the direction of air flow.
9. A humidifier as in claim 8 wherein the angle of the vanes from the vertical is about 30 degrees.
10. A humidifier which includes
    a housing having an air passage defined therein, said air passage including an enlarged scrubber area into which air is directed,
    venturi air inlet means for conveying air into the air passage,
    a water reservoir defined in the housing below the scrubber area and in communication with the venturi air inlet means,
    a series of vanes extending downwardly into the scrubber area at an acute angle from the vertical in the direction of air flow,
    means for heating water in the reservoir,
    means for drawing water from the reservoir and discharging the water into the air passage after the water has passes through the venturi air inlet means to thereby vaporize at least a portion of the water, and
    outlet means for conveying air and water vapor from the scrubber area.
11. A humidifier as in claim 10 wherein the vanes are formed to extend into the scrubber area alternately from opposite sides thereof to define a sinuous path of travel for the air flow.
12. A humidifier as in claim 11 wherein the air passage includes a venturi section, and wherein the means for drawing water includes a narrow channel extending between the reservoir and the venturi section.

* * * * *